United States Patent [19]

Dana

[11] Patent Number: 5,328,692

[45] Date of Patent: Jul. 12, 1994

[54] NEW LIQUID DENTIFRICE COMPOSITION

[76] Inventor: Dominique Dana, Le Mas du Cade Quartier des Plaine, 83440 Tanneron, France

[21] Appl. No.: 968,234

[22] Filed: Oct. 29, 1992

Related U.S. Application Data

[63] Continuation of Ser. No. 651,736, Feb. 7, 1991, abandoned, which is a continuation of Ser. No. 461,179, Jan. 5, 1990, abandoned.

[30] Foreign Application Priority Data

May 30, 1988 [FR] France .................. 88 07325

[51] Int. Cl.$^5$ .................. A61K 7/16; A61K 7/18; A61K 7/28
[52] U.S. Cl. .................. 424/401; 424/49; 424/50; 424/52
[58] Field of Search .................. 424/49.58, 401

[56] References Cited

U.S. PATENT DOCUMENTS

| | | | |
|---|---|---|---|
| 2,806,814 | 9/1957 | Richter | 424/54 |
| 3,683,065 | 8/1972 | Lauster | 424/57 |
| 3,947,567 | 3/1976 | Berg et al. | 424/49 |
| 4,108,978 | 8/1978 | Mazzanobile et al. | 424/52 |
| 4,335,102 | 6/1982 | Nakashima et al. | 424/52 |
| 4,363,794 | 12/1982 | Ochai et al. | 424/52 |
| 4,710,372 | 12/1987 | Scheller | 424/52 |
| 4,828,822 | 5/1989 | Muhlemann et al. | 424/52 |
| 4,950,479 | 8/1990 | Hill et al. | 424/49 |
| 5,009,881 | 4/1991 | Hill et al. | 424/49 |
| 5,032,387 | 7/1991 | Hill et al. | 424/49 |
| 5,057,306 | 10/1991 | Hill et al. | 424/49 |
| 5,057,307 | 10/1991 | Hill et al. | 424/49 |
| 5,057,308 | 10/1991 | Hill et al. | 424/52 |
| 5,057,309 | 10/1991 | Hill et al. | 424/52 |
| 5,057,310 | 10/1991 | Hill et al. | 424/52 |
| 5,078,788 | 1/1992 | Lin et al. | 424/54 |
| 5,154,915 | 10/1992 | Weber et al. | 424/54 |

FOREIGN PATENT DOCUMENTS

| | | | |
|---|---|---|---|
| 755331 | 10/1970 | Belgium | 424/50 |
| 133736 | 3/1985 | European Pat. Off. | 424/50 |
| 1467951 | 2/1969 | Fed. Rep. of Germany | 424/50 |
| 4675M | 1/1967 | France | 424/50 |
| 2051992 | 4/1971 | France | 424/50 |
| 2631823 | 12/1989 | France . | |
| 2651433 | 8/1991 | France . | |
| 56434 | 4/1982 | Japan | 424/50 |
| 686429 | 1/1953 | United Kingdom | 424/49 |
| 689679 | 4/1953 | United Kingdom | 424/49 |
| 1194885 | 6/1970 | United Kingdom | 424/49 |

OTHER PUBLICATIONS

American Chemical Society Abstract of Japanese Patent Publication No. 60130509, Jul. 12, 1985, "Dentifrices, Mouthwashes and Other Oral Compositions".

*Primary Examiner*—Shep K. Rose
*Attorney, Agent, or Firm*—Morgan & Finnegan

[57] ABSTRACT

Discloses a dentifrice composition having as the three main constituents an enzymatic complex, fluoroamines and Demethicone. A variety of optional constituents may also be present in the dentifrice. The dentifrice composition is applied to the teeth as a spray and is contained in a suitable container under pressure and provided with a spray nozzle so that it can be applied to the teeth and the interstices between them in the form of a jet of fine droplets.

10 Claims, No Drawings

NEW LIQUID DENTIFRICE COMPOSITION

This is a continuation of co-pending application Ser. No. 07/651,736, filed on Feb. 7, 1991 now abandoned which a continuation of co-pending application Ser. No. 07/461,179 filed Jan. 5, 1990, now abandoned.

This invention relates to a new dentifrice composition, a new galenic form thereof and a new way of using it.

Various dentifrice compositions in the form of a paste, a gel, a powder or a solution are known which are applied with a brush to the teeth. Dentifrice tubes provided with a measuring device also have been proposed, and some of which are filled with a propellent gas to force the dentifrice from the tubes but even in this latter case a toothbrush must always be used.

The use of a brush is always a constraint for many reasons. Inter alia, it is one reason why it is so difficult to train children to brush their teeth. For adults, on the other hand, it is impossible when away from home to clean one's teeth before a visit or after a meal. Where animals, such as dogs, are concerned, it is also not possible to clean their teeth.

This invention eliminates these drawbacks, providing a new liquid dentifrice composition contained in a container from which it is possible to eject it as a mist, or as fine droplets (spray), or as a pressure jet. The critical feature of this invention is the use as a spray of a liquid dentifrice solution, which is active against dental plaque, as well as being a preventive agent against dental decay and tartar formation, thanks to its components.

It should be noted that some dentifrice compositions have already been called "spray" composition; however this name was improper and deceptive previous to the instant invention, in so far as it is used in regard to such previous compositions for a system of ejection and approximate dosage of a paste or gel without any projection effects and simultaneous reduction of the composition to the form of fine particles projection effects. Consequently, a toothbrush is still needed in using such compositions. In some cases the proposed "sprays" were in liquid form which could be pulverized in the buccal cavity for purposes of buccal hygiene, such as hygienic lotions, instead of tooth care and decay prevention.

In contrast, the composition of the present invention, achieves such effects, by spraying a multitude of liquid particles upon all the teeth by simple, proper orientation of a jet of droplets on fine particles, to deposit upon all the teeth the components of the composition having a bactericidal action and/or a protective action against decay.

Such projection can be achieved by a vaporizer comprising a system for pumping the liquid and expelling it outwardly through a spraying nozzle.

It can also be obtained by using a propellent gas under pressure, such as, for example, nitrogen.

In both cases, according to a preferred modification of the invention, a jet of fine particle spray of liquid dentifrice is expelled under relatively high pressure, with a view to add to the effects resulting from the nature of the constituents, a mechanical effect i.e., cleaning of the teeth and the interstices between them.

There can be provided, in association with the container for the dentifrice composition, a further container containing rinse water which can also be expelled as a pressure jet. Such containers can be provided as interchangeable refills adaptable to the pressure expulsion system.

The system can be provided also with a swingable nozzle to allow the jet to be oriented in any proper direction.

The basic composition according to the invention comprises three main constituents:
- an enzymatic complex,
- fluorinated amines,
- Dimethicone, that is, dimethylpoly-siloxane, a preparation of homologous liquid methyl siloxane polymers and a vehicle therefor.

The enzymatic complex employed in the composition of the present invention is a known material (French Patent 89 11868) which is a combination of:
Dextranase
Mutanase
Glucose oxidase
Amyloglucosidase
Lactoperoxidase
Lysozyme
Lactoferrin The enzymatic complex exhibits natural bactericidal properties, as well as direct anti-dental plaque activity and some of the compounds thereof are extracted from saliva.

The fluoro-amines, that is, fluorinated amines, have an instantaneous effect, that is, in a time period of some seconds, to fix fluor, that is, fluorine, on the tooth enamel on the surface of the teeth, thus providing a preventive action against decay, as well as providing a protective film acting to inhibit the deposit of dental plaque. Exemplative of useful fluoro-amines are cetylamine fluoride and Bis-(Hydroxyethyl) Aminopropyl N-Hydroxyethyl octadecylamine dihydrofluoride.

On the other hand, Dimethicone also forms a film on the teeth and delays the appearance of tartar and the deposit of nicotine thereon, thus giving the teeth a smooth and shining appearance. All of the constituents in the composition of this invention are known to be innocuous to humans and animals and thus may be ingested without any harmful effects.

To those major constituents there can be added optional components such as:
Surfactive soap having a cleaning action
non-cariogen sugars (e.g. sorbitol or xylitol)
menthol as perfume
water, alcohol, preservative agents.

Generally a solution according to the invention comprises:
at least an antiseptic and/or antimicrobial agent
at least one agent acting against impurities such as tartar
at least a source of fluor
preferably a coloring agent, a perfume, an astringent and/or a shining agent
an solubilizing water.

As a non limitative example a dentifrice composition which meets the basic features of the invention, as recited above, and suitable for spraying upon the teeth as a nebulized jet.

The proportions of the components are given as weight percentage ranges:

EXAMPLE 1

| | |
|---|---|
| enzymatic complex | 1.5–10 |
| fluorinated amines (cetylamine fluoride) or (Bis (Hydroxyethyl) Aminopropyl N Hydroxyethyl octadecylamine dihydrofluoride) | 0.5–5 |
| Dimethicone | 0.1–3 |
| Polysorbate 80 | 0–3 |
| Polysorbate 20 | 0–3 |
| Saccharin | 0–2 |
| Glycerol | 0–30 |
| Sorbitol | 0–60 |
| Xylitol | 0–10 |
| Thiocyanate | 0–1 |
| colloidal Silica | 0–3 |
| Alcohol | 0–5 |
| $H_2O$ | 0–60 |
| Perfume (mint-anise) | 0.5–3 |
| Soaps | 0–10 |
| Preservative agents | 0–2 |
| Antiseptic | 0–2 |

According to a preferred embodiment, the composition of the invention comprises:

EXAMPLE 2

| | |
|---|---|
| enzymatic complex | 4.6 |
| fluorinated amines | 1.9 |
| Dimethicone | 1.5 |
| Polysorbate 80 | 1.4 |
| Polysorbate 20 | 1.4 |
| Saccharin | 0.15 |
| Glycerol | 10 |
| Sorbitol | 40 |
| Xylitol | 5 |
| Thiocyanate | 0.1 |
| colloidal Silica | 1 |
| water | QSP 30.0 |
| Perfume (mint-anise) | 1 |
| Soaps | 1.5 |
| Preservative agents | 0.15 |

The composition of the invention, contained in a small pocket device, such as a bottle, can or sealed plastic envelope or tube, can be used in any public location, at any convenient time, without a brush, even by children. It can also be commercialized in the form of a more bulky appliance such as a can or bottle installed in bathrooms.

It can also be used for cleaning animal teeth such as pets, e.g. dogs, which can obviously not use toothbrushes.

I claim:

1. Liquid dentifrice composition which can be applied to the teeth in the form of a spray and which can be ingested, charaterized in that it comprises as basic ingredients:
   a) at least one antiseptic and antimicrobial agent which is an enxymatic complex,
   b) at least one agent acting against tartar,
   c) at least one non-cariogenic sugar,
   d) at least one fluorine source,
and including a coloring agent, a perfume, an astringent, and a filmogen and shining agent, said composition also including sufficient water to form an aqueous solution, and which is contained in pressurized form in a container provided with a propellant gas under pressure or system for pumping the liquid, as well as spray nozzle means for expelling said solution as a spray mist or nebulized jet as a multitude of liquid droplet particles.

2. A liquid dentifrice composition according to claim 1 wherein component (b) is dimethylpolymer siloxane and component (d) is a fluorinated amine and which further includes at least one antiseptic, a coloring agent, a scent, an astringent, a filmogen agent and a polishing agent.

3. Composition according to claim 2, in which the components are present in the following weight percentages:

| | |
|---|---|
| antimicrobial agent and antidental plaque agent enzymatic complex | 1.5–10 |
| fluorinated amine | 0.5–5 |
| dimethylpolysiloxane | 0–3 |
| Polysorbate 80 | 0–3 |
| Polysorbate 20 | 0–3 |
| Saccharin | 0–2 |
| Glycerol | 0–30 |
| Sorbitol | 0–60 |
| Xylitol | 0–10 |
| Thiocyanate | 0–1 |
| colloidal Silica | 0–3 |
| Alcohol | 0–5 |
| $H_2O$ | 0–60 |
| scent | 0.5–3 |
| Soaps | 0–10 |
| Preservative agents | 0–2 |
| Antiseptic | 0–2. |

4. Composition according to claim 2, in which the components are present in the following weight percentages:

| | |
|---|---|
| antimicrobial agent and antidental plaque agent enzymatic complex | 4.6 |
| fluorinated amines | 1.9 |
| dimethylpolysiloxane | 1.5 |
| Polysorbate 80 | 1.4 |
| Polysorbate 20 | 1.4 |
| Saccharin | 0.15 |
| Glycerol | 10 |
| Sorbitol | 40 |
| Xylitol | 5 |
| Thiocyanate | 0.1 |
| colloidal Silica | 1 |
| water | 30.3 |
| scent | 1 |
| Soaps | 1.5 |
| Preservative agent | 0.15. |

5. Composition according to claim 2, in which the fluorinated amine is cetylamine fluoride.

6. Composition according to claim 2, in which the fluorinated amine is Bis (hydroxyethyl) aminopropyl N hydroxyethyl-octadecylamine dihydrofluoride.

7. Composition according to claim 3, in which the fluorinated amine is cetylamine fluoride.

8. Composition according to claim 3, in which the fluorinated amine is Bis(hydroxyethyl) aminopropyl N hydroxyethyl-octadecylamine dihydrofluoride.

9. A liquid dentifrice composition comprising:
   (a) an antimicrobial agent and an antidental plaque agent which is an enzymatic complex;
   (b) an anti-tartar agent;
   (c) at least one non-cariogenic sugar;
   (d) at least one fluorine source; and
   (e) sufficient water to form an aqueous solution of elements (a)–(d) such that said solution may be sprayed as a spray, mist or nebulized jet as a multitude of liquid droplet particles.

10. Nebulizing jet spray apparatus containing the composition of claim 9, under pressure of a propellant gas, or system for pumping the liquid in a container provided with a spraying nozzle means for expelling said composition under the form of a pressure jet as a multitude of liquid droplet particles, spray or mist.

* * * * *